United States Patent
Hu et al.

(10) Patent No.: US 10,803,144 B2
(45) Date of Patent: Oct. 13, 2020

(54) PREDICTING DRUG-DRUG INTERACTIONS BASED ON CLINICAL SIDE EFFECTS

(71) Applicant: INTERNATIONAL BUSINESS MACHINES CORPORATION, Armonk, NY (US)

(72) Inventors: Jianying Hu, Bronx, NY (US); Robert K. Sorrentino, Rye Brook, NY (US); Fei Wang, Ossining, NY (US); Ping Zhang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 661 days.

(21) Appl. No.: 14/270,498

(22) Filed: May 6, 2014

(65) Prior Publication Data

US 2015/0324693 A1 Nov. 12, 2015

(51) Int. Cl.
*G01N 33/48* (2006.01)
*G06F 19/00* (2018.01)
*G06N 5/04* (2006.01)
*G06N 20/00* (2019.01)

(52) U.S. Cl.
CPC ........ *G06F 19/326* (2013.01); *G06F 19/3456* (2013.01); *G06N 5/04* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 6,128,620 A | 10/2000 | Pissanos et al. | |
| 7,698,157 B2 | 4/2010 | Ghouri | |
| 8,000,977 B2 | 8/2011 | Achan | |
| 8,311,851 B2 | 11/2012 | Patterson et al. | |
| 8,483,872 B2 | 7/2013 | Ratnakar | |
| 2004/0213448 A1* | 10/2004 | Jou | G07D 7/00 382/135 |
| 2004/0242454 A1 | 12/2004 | Gallant | |
| 2006/0145856 A1* | 7/2006 | Tethrake | G06Q 10/08 340/572.1 |
| 2007/0136214 A1* | 6/2007 | Eskandari | B41J 2/17509 705/408 |
| 2008/0004913 A1 | 1/2008 | Sayre | |
| 2010/0128296 A1* | 5/2010 | Denniston, Jr. | G06F 3/03545 358/1.13 |
| 2013/0179091 A1 | 11/2013 | Jackson et al. | |
| 2013/0332187 A1 | 12/2013 | Maman et al. | |

FOREIGN PATENT DOCUMENTS

| | | |
|---|---|---|
| CA | 2800722 A1 | 7/2013 |
| EP | 2339488 A1 | 6/2011 |

OTHER PUBLICATIONS

Li, Fan, and Yiming Yang. "A loss function analysis for classification methods in text categorization." In Proceedings of the 20th International Conference on Machine Learning (ICML-03) (2003) pp. 472-479.*

Cover, Thomas, and Peter Hart. "Nearest neighbor pattern classification." IEEE transactions on information theory 13, No. 1 (1967): pp. 21-27.*

Mangu, L., Brill, E. and Stolcke, A., 1999. Finding consensus among words: Lattice-based word error minimization. In Sixth European Conference on Speech Communication and Technology.*

Huang, J., et al. "Systematic Prediction of Pharmacodynamic Drug-Drug Interactions Through Protein-Protein-Interaction Network" PLOS Computational Biology, vol. 9, No. 3. Mar. 2013. pp. 1-9.

Kuhn, M., et al. "A Side Effect Resource to Capture Phenotypic Effects of Drugs" Molecular Systems Biology, vol. 6, No. 343, Jan. 2010. pp. 1-6.

Lin, J. "Sense and Nonsense in the Prediction of Drug-Drug Interactions" Current Drug Metabolism, vol. 1, No. 4. Dec. 2000. pp. 305-331.

Percha, B., et al. "Informatics Confronts Drug—Drug Interactions" Trends in Pharmacological Sciences. vol. 34, No. 3. Mar. 2013. pp. 178-184.

Samwald, M. et al. "Linked Open Drug Data for Pharmaceutical Research and Development" Journal of Cheminformatics. vol. 3, No. 19. May 2011. pp. 1-6.

Vilar, S., et al. "Drug-Drug Interaction Through Molecular Structure Similarity Analysis" J Am Med Inform Association, vol. 19, No. 6. Nov. 2012. pp. 1066-1074.

Vilar, S., et al. "Detection of Drug-Drug Interactions by Modeling Interaction Profile Fingerprints" PLOS One, vol. 8, No. 13. Mar. 2013. pp. 1-11.

\* cited by examiner

*Primary Examiner* — Anna Skibinsky
(74) *Attorney, Agent, or Firm* — Tutunjian & Bitetto, P.C.; Kristofer Haggerty

(57) ABSTRACT

A processor-implemented method, computer program product and system are provided for predicting drug-drug interactions based on clinical side effects. The method includes constructing a drug-drug interactions training dataset that includes pharmaceutical, pharmacokinetic or pharmacodynamics drug-drug interactions from multiple data sources for each of a plurality of drugs. The method also includes constructing side effect features for each of the drugs from side effects associated with the drugs. The method further includes building, using the drug-drug interactions training dataset, a drug-drug interactions classifier that predicts adverse drug-drug interactions for drug pairs derivable from the drugs. The method additionally includes for each of the side effects, building a two-by-two table using the side effect features, and performing a Fisher's exact test using the two-by-two table to determine whether a given one of side effects is differentially shown between positive predicted drug-drug interactions and negative predicted drug-drug interactions.

19 Claims, 7 Drawing Sheets

PREDICTING DRUG-DRUG INTERACTIONS BASED ON CLINICAL SIDE EFFECTS

BACKGROUND

Technical Field

The present invention relates generally to medicine and, in particular, to predicting drug-drug interactions based on clinical side effects.

Description of the Related Art

Adverse drug-drug interactions (DDIs) are serious health threats that can result in significant morbidity and mortality. Recent estimates indicate that DDIs cause nearly 74,000 emergency room visits and 195,000 hospitalizations each year in the USA. Current approaches to drug-drug interaction (DDI) discovery, which include Phase IV clinical trials and post-marketing surveillance, are insufficient for detecting many DDIs and do not alert the public to potentially dangerous DDIs before a drug enters the market.

DDIs can be categorized into three types: pharmaceutical; pharmacokinetic (PK); and pharmacodynamic (PD). Current studies mainly focused on pharmaceutical and PK DDIs and established experimental and simulation approaches to test for metabolic or transporter-based drug interactions. However, a large number of DDIs cannot be explained at the PK or pharmaceutical levels and are supposed to be potential PD DDIs. Many of these interactions are not easily discernible because the endpoint is often a potentially serious adverse event rather than a measurable change in the concentration of the drug.

Moreover, current DDIs predictions use molecular structure and/or interaction profile. Such information is (1) with translational issue and (2) lacking clinical explanations.

SUMMARY

According to an aspect of the present principles, a processor-implemented method is provided for predicting drug-drug interactions based on clinical side effects. The method includes constructing a drug-drug interactions training dataset that includes pharmaceutical, pharmacokinetic or pharmacodynamics drug-drug interactions from multiple data sources for each of a plurality of drugs. The method further includes constructing side effect features for each of the plurality of drugs from side effects associated with the plurality of drugs. The method also includes building, using the drug-drug interactions training dataset, a drug-drug interactions classifier that predicts adverse drug-drug interactions for drug pairs derivable from the plurality of drugs. The method additionally includes, for each of the side effects, building a two-by-two table using the side effect features, and performing a Fisher's exact test using the two-by-two table to determine whether a given one of side effects is differentially shown between positive predicted drug-drug interactions and negative predicted drug-drug interactions.

According to another aspect of the present principles, there is provided a computer program product for predicting drug-drug interactions based on clinical side effects, the computer program product comprising a computer readable storage medium having program instructions embodied therewith, the program instructions executable by a computer to cause the computer to perform a method. The method includes constructing a drug-drug interactions training dataset that includes pharmaceutical, pharmacokinetic or pharmacodynamics drug-drug interactions from multiple data sources for each of a plurality of drugs. The method also includes constructing side effect features for each of the plurality of drugs from side effects associated with the plurality of drugs. The method further includes building, using the drug-drug interactions training dataset, a drug-drug interactions classifier that predicts adverse drug-drug interactions for drug pairs derivable from the plurality of drugs. The method additionally includes, for each of the side effects, building a two-by-two table using the side effect features, and performing a Fisher's exact test using the two-by-two table to determine whether a given one of side effects is differentially shown between positive predicted drug-drug interactions and negative predicted drug-drug interactions.

According to still another aspect of the present principles, there is provided a system for predicting drug-drug interactions based on clinical side effects. The system includes a drug-drug interactions training dataset constructor for constructing a drug-drug interactions training dataset that includes pharmaceutical, pharmacokinetic or pharmacodynamics drug-drug interactions from multiple data sources for each of a plurality of drugs. The system also includes a side effect features constructor for constructing side effect features for each of the plurality of drugs from side effects associated with the plurality of drugs. The system further includes a drug-drug interactions classifier builder for building, using the drug-drug interactions training dataset, a drug-drug interactions classifier that predicts adverse drug-drug interactions for drug pairs derivable from the plurality of drugs. The system additionally includes a two-by-two table builder for building, for each of the side effects, a two-by-two table using the side effect features. The system also includes a Fisher's exact tester having a processor for performing a Fisher's exact test using the two-by-two table to determine whether a given one of side effects is differentially shown between positive predicted drug-drug interactions and negative predicted drug-drug interactions.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present principles are directed to predicting drug-drug interactions based on clinical side effects.

Figure 1:
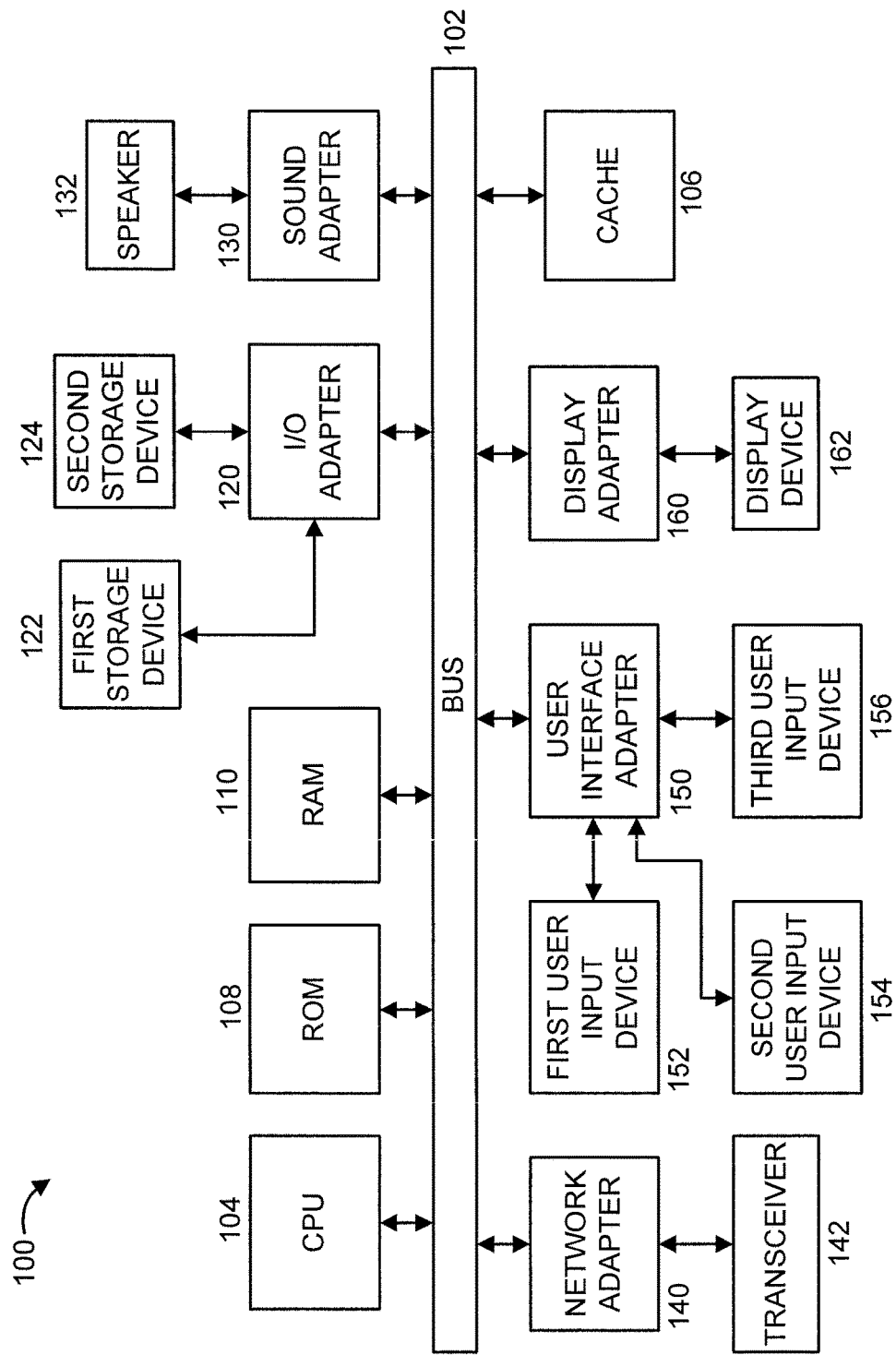
FIG. 1 shows an exemplary processing system 100 to which the present principles may be applied, in accordance with an embodiment of the present principles.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operative coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
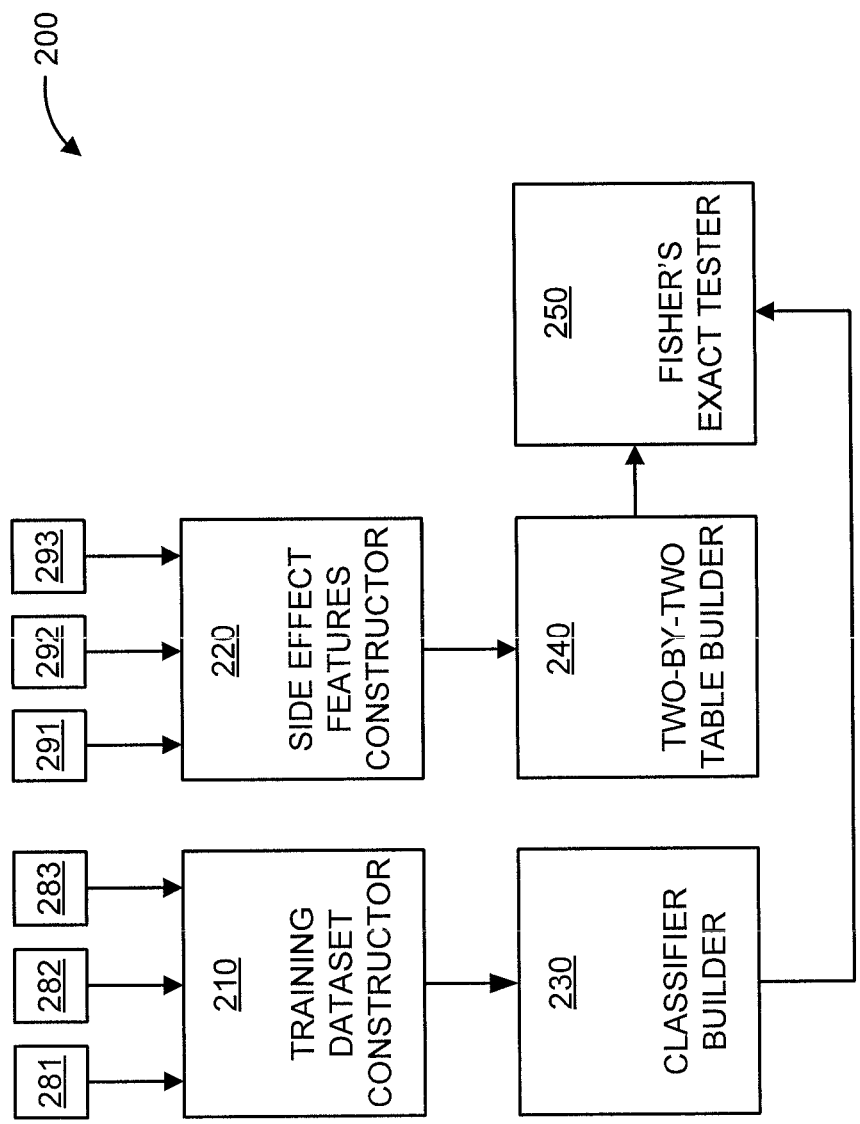
FIG. 2 shows a system 200 for predicting drug-drug interactions based on clinical side effects, in accordance with an embodiment of the present principles.

Moreover, it is to be appreciated that system 200 described below with respect to FIG. 2 is a system for implementing respective embodiments of the present principles. Part or all of processing system 100 may be implemented in one or more of the elements of system 200.

Figure 3:
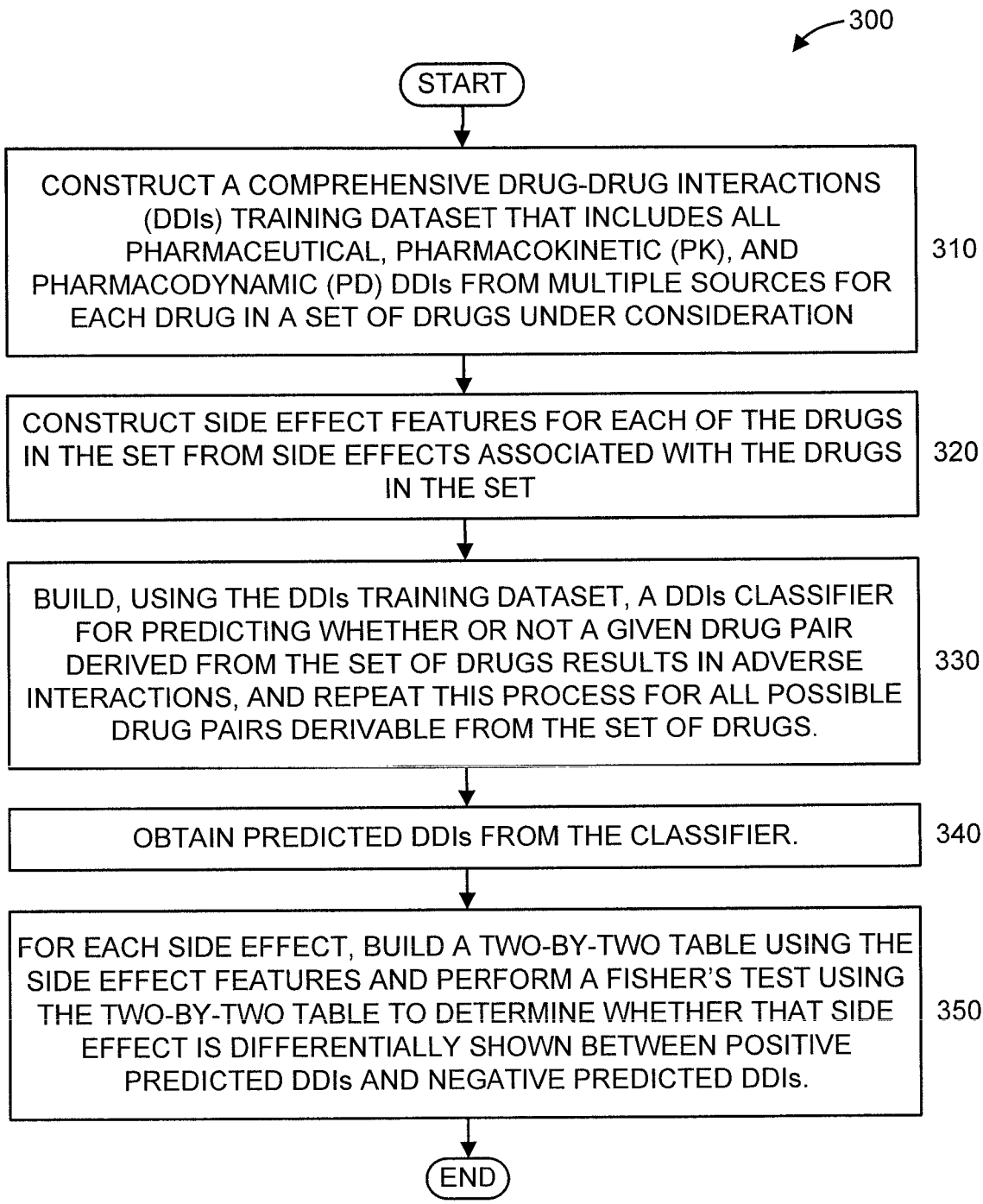
FIG. 3 shows a method 300 for predicting drug-drug interactions based on clinical side effects, in accordance with an embodiment of the present principles.
Figure 4:
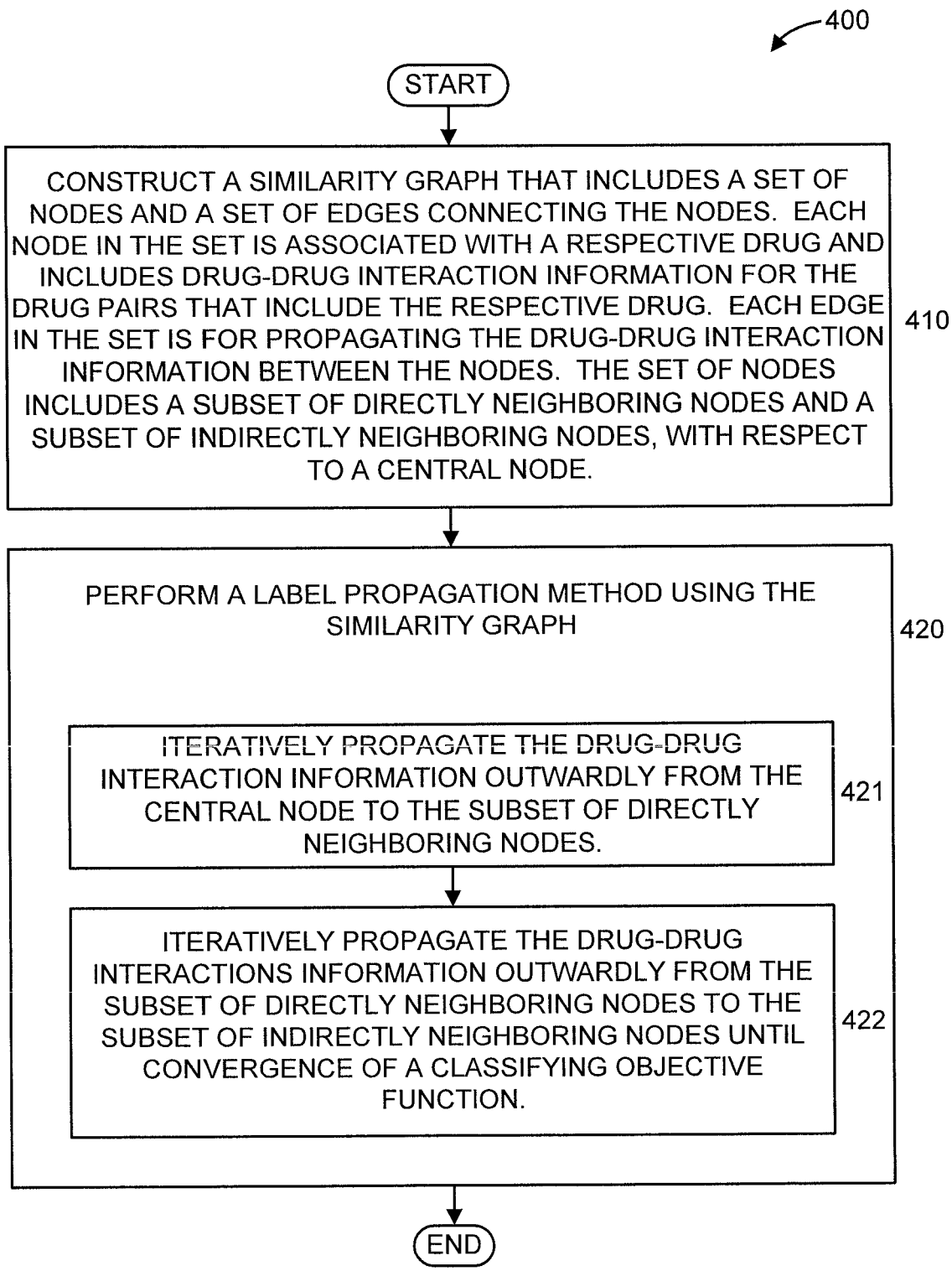
FIG. 4 shows a method 400 for propagating labels in a similarity graph to predict drug-drug interactions based on clinical side effects, in accordance with an embodiment of the present principles.

Further, it is to be appreciated that processing system 100 may perform at least part of the method described herein including, for example, at least part of method 300 of FIG. 3 and/or at least part of method 400 of FIG. 4. Similarly, part or all of system 200 may be used to perform at least part of method 300 of FIG. 3 and/or at least part of method 400 of FIG. 4.

FIG. 2 shows a system 200 for predicting drug-drug interactions based on clinical side effects, in accordance with an embodiment of the present principles. The system 200 includes a drug-drug interactions (DDIs) training dataset constructor 210, a side effect features constructor 220, a drug-drug interactions (DDIs) classifier builder 230, a two-by-two table builder 240, and a Fisher's exact tester 250. The system 200 interacts with and/or otherwise receives information from multiple data sources. For example, in the embodiment of FIG. 2, the DDIs training dataset constructor 210 receives information from multiple data sources 281, 282 and 283, and the side effect features constructor 220 receives information from multiple data sources 291, 292, and 293. In an embodiment, the DDIs training dataset constructor 210 includes a memory 211 for storing the dataset. Of course, in other embodiments, the memory 211 can be implemented as a separate device from the DDIs training dataset constructor 210 or can be part of another element of system 200. Moreover, in the embodiment of FIG. 2, the Fisher's exact tester 250 includes a processor 251. Of course, in other embodiments, the processor 251 can be implemented as a separate device from the Fisher's exact tester 250 or can be part of another element of system 200. These and other variations of system 200 are readily determined by one of ordinary skill in the art, given the teachings of the present principles provided herein, while maintaining the spirit of the present principles. The elements of FIG. 2 are described in further detail herein below.

As noted above, DDIs can be categorized into three types: pharmaceutical; pharmacokinetic (PK); and pharmacodynamic (PD). Pharmaceutical DDIs occur because of a physical or chemical incompatibility. PK DDIs occur whereby a drug is affecting the processes by which another drug is absorbed, distributed, metabolized or excreted (ADME). PD DDIs occur where the effects of one drug are modified by the effect of another on its site of action or by affecting the same or cross-talking signaling pathways.

FIG. 3 shows a method 300 for predicting drug-drug interactions based on clinical side effects, in accordance with an embodiment of the present principles.

At step 310, construct a comprehensive drug-drug interactions (DDIs) training dataset that includes all pharmaceutical, pharmacokinetic (PK), and pharmacodynamic (PD) DDIs from multiple data sources for each drug in a set of drugs under consideration. In an embodiment, the multiple data sources can include, but are not limited to, the following: clinical trials; drug development information; empirical information; a drug bank; drug label information; an adverse event reporting system (e.g., the FDA Adverse Event Reporting System information (FAERS)); and text mining from scientific documents (e.g., search tool for interactions of chemicals (STITCH)). Step 310 can be performed by, e.g., the drug-drug interactions training dataset constructor 210.

At step 320, construct side effect features for each of the drugs in the set from side effects associated with the drugs in the set. In an embodiment, all drugs' side effects, from which the side effect features are constructed, come from one or more of the following sources: clinical trials; drug development; empirical information; FDA drug label (SIDER and DAILYMED®); FDA Adverse Event Reporting System (FAERS); and real-world evidence. Step 320 can be performed by, e.g., the side effect features constructor 220.

At step 330, build, using the DDIs training dataset, a DDIs classifier for predicting whether or not a given drug pair derived from the set of drugs results in adverse interactions, and repeat this process for all possible drug pairs derivable from the set of drugs. In an embodiment, the features used for building the classifier can include, but are not limited to, the following: drug's clinical side effect keywords; and other drug properties (e.g., chemical structures, protein targets, and so forth). Step 330 can be performed by, e.g., the drug-drug interactions classifier builder 230.

At step 340, obtain predicted DDIs from the classifier. Step 330 can be performed by, e.g., the drug-drug interactions classifier builder 230.

At step 350, for each side effect, build a two-by-two table using the side effect features and perform a Fisher's exact test using the two-by-two table to determine whether that side effect is differentially shown between positive predicted DDIs and negative predicted DDIs. Step 350 can be performed by, e.g., the two-by-two table builder 240, and the Fisher's exact tester 250.

Regarding step 350, we provide the following. The term "positive predicted DDIs" refers to drugs pairs that cannot be taken together. In contrast, the term "negative predicted DDIs" refers to drugs pairs that may be safe to use together. The analysis shows that if both drugs of the drug pair have the same side effect in the list (e.g., retinal bleeding), it seems that the drug pair is not safe, as the drug pair results in DDIs.

Further regarding step 350, an exemplary format of the two-by-two table is shown in TABLE 1 as follows:

TABLE 1

|  | DDI+ | DDI− |
| --- | --- | --- |
| side effect+ | tp | fp |
| side effect− | fn | tn | where "DDI+" denotes that the drug pair has a DDI, "DDI−" denotes that the drug pair does not have a DDI, "side effect +" denotes that each drug of the drug pair has this side effect, "side effect −" denotes that none of the drugs in the drug pair have this side effect, "tp" denotes a true positive and means that the drug pair has this side effect and has a DDI, "fp" denotes a false positive and means that the drug pair has this side effect and does not have a DDI, "fn" denotes a false negative and means that the drug pair does not have this side effect and has a DDI, and "tn" denotes a true negative and means that the drug pair does not have this side effect and does not have a DDI.

A description will now be given of at least some advantageous and novel features of the present principles, in accordance with an embodiment of the present principles. As a first feature, we use clinical phenotypic information (e.g., side effects) to conduct a drug network. Then we predict DDIs based on the drug network inference.

As a second feature, our proposed method takes into account high-order network structure. "High-order" means in a network two nodes do not directly link to each other, but can visit each other by going through other bridge nodes.

As a third feature, our proposed multitask label propagation approach provides DDI profiles of multiple drugs simultaneously.

Side effects are effects after taking a medicine, which are other than the intended therapeutic effects. Label side effects means the side effects are recorded in drug labels (for example, but not limited to, SIDER database, DAILYMED®, and so forth). FDA side effects means the side effects are recorded in, for example, but not limited to, the FDA Adverse Event Reporting System (FAERS). Consider, for example, the drug Ibuprofen as an example, DAILYMED® records its 249 types of label side effects (e.g., abdominal discomfort, confusion, dry mouth, vomiting, and weight loss), and FAERS records its 728 types of FDA side effects (e.g., anxiety, ear ache, fatigue, tooth loss, sleep disorder).

The side effect profile similarity score is in the [0, 1] range. Each drug d was represented by a multiple dimensional binary side effect profile e(d) whose elements encode for the presence or absence of each of the side effect key words by 1 or 0 respectively. The pairwise side effect similarity between two drugs $d_x$ and $d_y$ is computed as the Tanimoto coefficient of their fingerprints as follows:

$$sim(d_x, d_y) = \frac{e(d_x) \cdot e(d_y)}{|e(d_x)| + |e(d_y)| - e(d_x) \cdot e(d_y)}$$

where $|e(d_x)|$ and $|e(d_y)|$ are the counts of side effect keywords for drugs $d_x$ and $d_y$, respectively. The dot product $e(d_x) \cdot e(d_y)$ represents the number of side effects shared by the two drugs. The fingerprint of a drug is a bitstring based on its structure, constructed such that structurally similar drugs will have similar fingerprints. Consider, for example, the following two popular drugs Ibuprofen and Aspirin. For label side effect, the intersection size of their side effect profiles is 22, and the union size of their side effect profiles is 254, thus the label side effect similarity score of Ibuprofen and Aspirin is 0.087. For FDA side effect, the intersection size of their side effect profiles is 161, and the union size of their side effect profiles is 925, thus the FDA side effect similarity score of Ibuprofen and Aspirin is 0.174.

Our objective is to minimize a loss function, that is, the objective function also referred to herein as the classifying function. The loss function for one step is as follows:

$$f_k^{(i)}(t+1) = \alpha \sum_j w_{ij} f_j^{(i)}(t) + (1-\alpha) y_k^{(i)},$$

where α is a parameter that determines the influence of a node's neighbors relative to its provided label, $w_{ij}$ is the weight of the edge between node i and its neighbor j, and y is the label vector. The first term of the loss function, namely $$\alpha \sum_j w_{ij} f_j^{(i)}(t),$$

is the smoothness constraint, which means that a good classifying function should not change too much between nearby points. The second term of the loss function, namely $(1-\alpha)y_k^{(i)}$, is the fitting constraint, which means a good classifying function should not change too much from the initial label assignment. The trade-off between these two competing constraints is captured by a positive parameter which between 0 and 1.

In order to minimize the loss function, we need the following iterative procedure. At each step, each drug "propagates" its interaction information with query drugs to its direct neighborhood (i.e., directly neighboring nodes), and iterates this process until convergence. Let y be the initial DDIs vector which includes the known interaction information and let f be the predicted DDIs.

FIG. 4 shows a method 400 for propagating labels in a similarity graph to predict drug-drug interactions based on clinical side effects, in accordance with an embodiment of the present principles.

Figure 5:
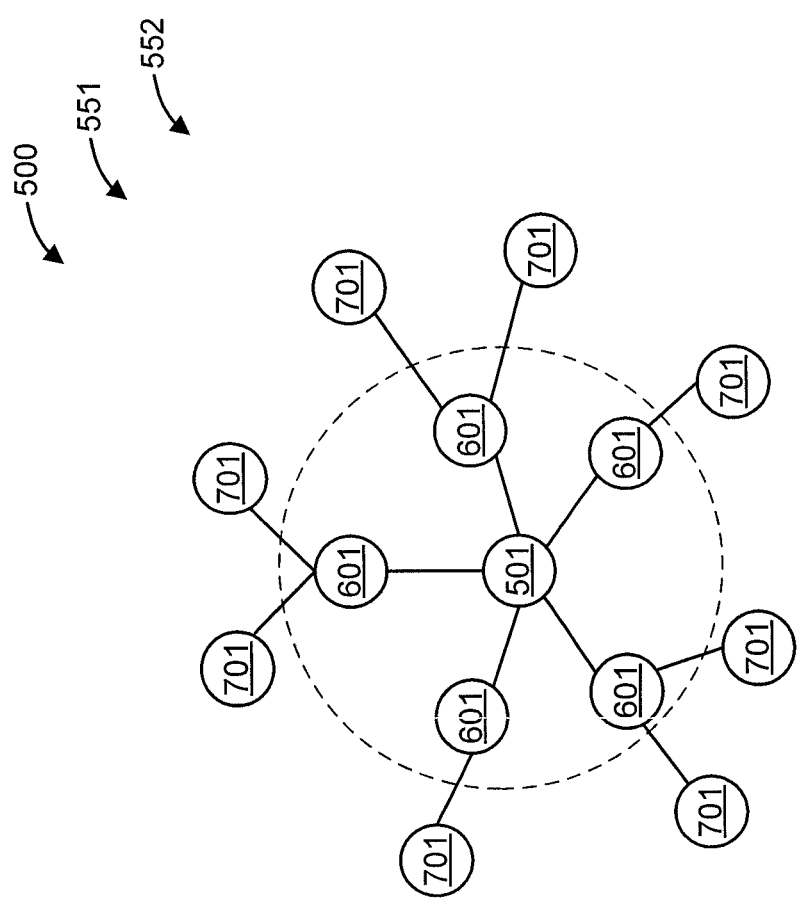
FIG. 5 shows a drug similarity graph 500 before label propagation, in accordance with an embodiment of the present principles.
Figure 6:
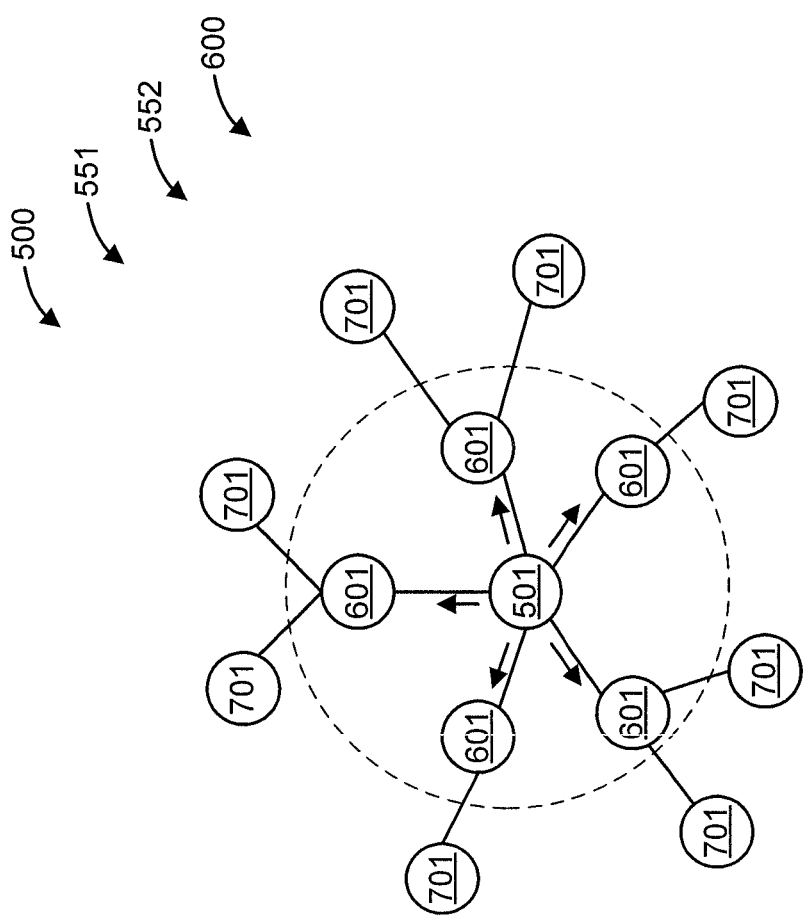
FIG. 6 shows the drug similarity graph 500 of FIG. 1 after a first round 600 of label propagation, in accordance with an embodiment of the present principles.
Figure 7:
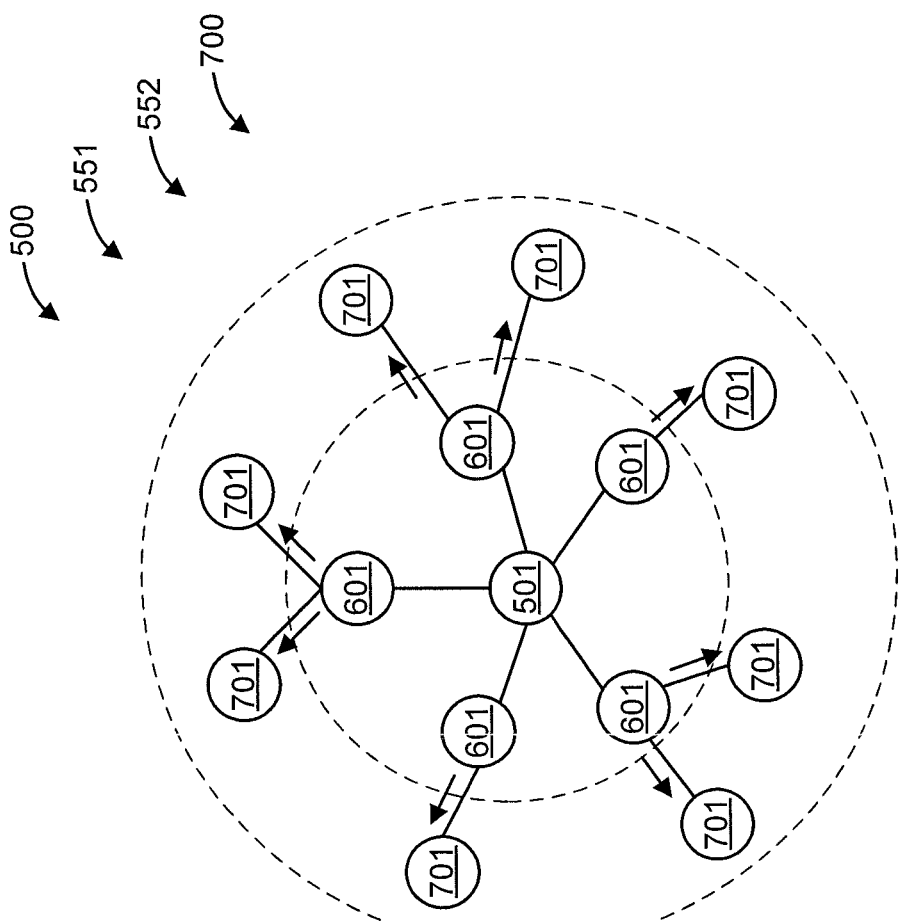
FIG. 7 shows the similarity graph 500 of FIG. 5 after a second round 700 of propagation, in accordance with an embodiment of the present principles.

For illustrative purposes, method 400 will now be described with respect to FIGS. 5-7. FIGS. 5-7 include a drug similarly graph 500 to which the present principles can be applied. In particular, FIG. 5 shows a drug similarity graph 500 before label propagation, in accordance with an embodiment of the present principles. FIG. 6 shows the drug similarity graph 500 of FIG. 1 after a first round 600 of label propagation, in accordance with an embodiment of the present principles. FIG. 7 shows the similarity graph 500 of FIG. 5 after a second round 700 of propagation, in accordance with an embodiment of the present principles.

Referring to FIGS. 4-7, at step 410, construct a similarity graph 500 that includes a set 551 of nodes and a set 552 of edges connecting the nodes. Each node in the set 551 is associated with a respective drug and includes drug-drug interactions information for the drug pairs that include the respective drug. Each edge in the set 552 is for propagating the drug-drug interactions information between the nodes. In an embodiment, the similarity graph 500 is constructed to have, from the set 551 of nodes, a central node 501, a subset 601 of directly neighboring nodes with respect to the central node 501, and a subset 701 of indirectly neighboring nodes with respect to the central node 501 (see, e.g., FIGS. 5-7). While one or more embodiments here show propagation commencing from a central node (i.e., central node 501), in other embodiments, propagation can begin from a non-central node. However, in such embodiments, the essence of propagation is the same in that propagation begins from a starting node to the directly neighboring nodes (with respect to the central node) and thereafter from the directly neighboring nodes to the indirectly neighboring nodes (with respect to the central node). These and other variations of the present principles are readily determined from the teachings of the present principles provided herein, while maintaining the spirit of the present principles. In FIGS. 5-7, each of the nodes included in the subset 601 is designated by the reference numeral 601, and each of the nodes included in the subset 701 is designated by the reference numeral 701.

In the following steps, the method 400 iteratively propagates the drug-drug interactions information outwardly from the central node 501 to the subset 601 of directly neighboring nodes and thereafter to the subset 701 of indirectly neighboring nodes until convergence of the classifying objective function.

At step 420, perform a label propagation method using the similarity graph. Step 420 includes steps 421 and 422.

At step 421, iteratively propagate the drug-drug interactions information outwardly from the central node 501 to the subset 601 of directly neighboring nodes.

At step 422, iteratively propagate the drug-drug interactions information outwardly from the subset 601 of directly neighboring nodes to the subset 701 of indirectly neighboring nodes until convergence of a classifying objective function.

Thus, referring to FIG. 5, in graph 500, we only have the central node 501 which has a known DDIs profile, thus $f^0=y$, where f denotes the score of the central node 501 prior to the first round 600, and y denotes a label vector. Thus, $y_i=1$ denotes that drug i is known to have a DDI with the reference drug and $y_i=0$ otherwise. In graph 500, the subset 601 of directly neighboring nodes and the subset 701 of indirectly neighboring nodes are not yet implicated in method 400 of FIG. 4, as FIG. 5 corresponds to step 410 of FIG. 4.

Referring to FIG. 6, we note that the same corresponds to step 421 of FIG. 4. In the first round 600 of label propagation, the central node 501 propagates its interaction information with query drugs to the directly neighboring nodes 601 in the dashed circle 699. Let $w_i$ be the weight between the central node 501 and its i-th neighbor 601 (the weight can be calculated, for example, but it not limited to, the drug's side effect profiles), thus $$f^1 = \alpha \sum_i w_i f^0 + (1-\alpha)y,$$

where $f^1$ is the score of a given directly neighboring node after the first round 600, and $0<\alpha<1$ is the fraction of label information that the neighbors receive from the central node 501.

Referring to FIG. 7, we note that the same corresponds to step 422 of FIG. 4. In the second round 700 of label propagation, the subset 601 directly neighboring nodes propagate their interaction information with query drugs to the subset 701 of indirectly neighboring nodes in the outer dashed circle 799. Similarly, let $w_j$ be the weight between the subset 601 of directly neighboring nodes and their j-th neighbor, thus $$f^2 = \alpha \sum_j w_j f^1 + (1-\alpha)y,$$

where $f^2$ is the score of a given indirectly neighboring node after the second round 700.

The method 400 iterates this label propagation process until convergence. We construct a symmetrically normalized weighted network adjacency matrix $W \in R^{n \times n}$, where (i, j)-th element of W is the weight between nodes i and j which is calculated from their side effect profiles. We note that W is a normalized form of matrix A. Then we can rewrite our iteration equation as follows: $f^{t+1}=\alpha W f^t +(1-\alpha)y$. Considering that the initial condition is $f^0=y$, we have the following equation:

$$f^t = (\alpha W)^{t-1} y + (1-\alpha) \sum_{i=0}^{t-1} (\alpha W)^i y.$$

We can prove that the sequence $f^t$ will converge to $$f^* = \lim_{t \to \infty} f^t = (1-\alpha)(I - \alpha W)^{-1} y.$$

In an embodiment, our method uses $f^*$ as DDIs predictions.

From the iterative solution, we can conclude that our method considers the high-order network structure, which is more optimal than the methods that only consider the first-order network structure.

A further description will now be provided of the label propagation method, in accordance with an embodiment of the present principles.

In an embodiment, we use an undirected weighted network with n nodes where some of them can be labeled (e.g., as positive), and we estimate the labels of the rest unlabeled nodes. We treat different drugs as nodes on the network, and compute the edge weights on the network with drug similarities evaluated using the aforementioned similarity method. For each drug, we label all other drugs in the network as positive if they are known to have a DDI with this drug, and utilize label propagation on such drug network to estimate the possibility that the unlabeled drugs will have a DDI with this drug. Also, for each drug, we label all other drugs in the network as negative if they are known to not have a DDI with this drug, and utilize label propagation on such drug network to estimate the possibility that the unlabeled drugs will not have a DDI with this drug.

More concretely, we represent the input drug network using an n×n affinity matrix A where $A_{ij} \geq 0$ is the similarity between drug i and j. As noted above, for each drug, we construct a label vector $y \in \{0,1\}^n$ over the network, where $y_i = 1$ if drug i is known to have a DDI with the reference drug, and $y_i = 0$ otherwise. With those notations, label propagation assigns scores (which indicate the possibility that each drug will have a DDI with the reference drug) to drug nodes by an iterative procedure which propagates evidence out from positive nodes through the edges in the network. In particular, in each iteration of label propagation, the score of node i, given by $f_i$, is updated by taking a weighted sum of the scores of i's neighbors at the previous iteration, along with i's initial label. In an embodiment, we can ensure convergence of the updates by normalizing the original affinity matrix A so that the row sum is one. In an embodiment, we can use, for example, a Bregmanian Bi-Stochastication (BBS) algorithm for such normalization and denote the normalized matrix as W. One nice aspect of BBS is that the resultant normalized matrix is still symmetric. Of course, normalization is not limited to using BBS and, thus, other approaches can also be used.

Using W, we propagate labels from the labeled drug nodes to the unlabeled nodes. In each propagation iteration, the estimated score of each drug node "absorbs" a portion ($\alpha$) of the label information from its neighborhood, and retains a portion ($1-\alpha$) of its initial label information. The updating rule for node i is given by $$f_i^{after} \leftarrow \alpha \sum_{j=1}^{n} W_{ij} f_j^{before} + (1-\alpha) y_i.$$

In this formula, $0 < \alpha < 1$ is a parameter that determines the influence of a node's neighbors relative to its provided label. By concatenating the predicted scores for all drug nodes, we can obtain the matrix form of the updating rule as follows: $f^{after} \leftarrow \alpha W f^{before} + (1-\alpha) y$. It can be shown that after t iterations, the predicted score vector $f^t$ can be written as follows:

$$f^t = (\lambda W)^{t-1} y + (1-\lambda) \sum_{i=0}^{t-1} (\lambda W)^i y.$$

Since $W_{ij} \geq 0$, and $\Sigma_j W_{ij} = 1$, the spectral radius of W, or $\rho(W) \leq 1$. In additional, $0 < \alpha < 1$, thus $$\lim_{t \to \infty} (\alpha W)^{t-1} = 0 \text{ and}$$

$$\lim_{t \to \infty} \sum_{i=0}^{t-1} (\alpha W)^i = (I - \alpha W)^{-1}$$

where I is the identity matrix of order n. Therefore, $f^t$ will eventually converge to $$f = \lim_{t \to \infty} f^t = (1-\alpha)(I - \alpha W)^{-1} y.$$

In our scenario, there are 11 tasks, i.e., we want to predict the DDI profile for each drug. To achieve this, in an embodiment, we can first concatenate the initial label vector y for each drug into an initial label matrix Y, where its (i, j)-th entry is 1 if drug i interacts with drug j, and 0 means there is no known interaction between drug i and drug j. Then we can get all the DDI predictions in one-shot as follows:

$$F = (1-\alpha)(I - \alpha W)^{-1} Y.$$

Actually the converged solution for label propagation for the whole graph can also be obtained by minimizing the following objective function:

$$J = \alpha \text{tr}(F(I-W)F) + (1-\alpha) \|F-Y\|_F^2 \qquad (1).$$

In this formula, tr(•) denotes the trace or a matrix, and $\|\bullet\|_F$ denotes Frobenius norm of a matrix. The first term of Equation (1) is a smoothness term, which assumes that the prediction should not vary too much on the intrinsic network. In our case, it means that the predicted DDI score for any reference drugs should change smoothly over the drug network. This coincides with our drug similarity assumption: similar drugs tend to have similar DDI effects. The second term of Equation (1) is the fitting term, which restricts the predicted DDI scores to be close to their initial values. The trade-off between those two competing terms is captured by a nonnegative parameter a between 0 and 1. As Equation (1) is convex with respect to F, we can get its global optimum by setting the first order derivative of J with respect to F to zero as follows:

$$\partial J / \partial F = 2(\alpha(I-W)F + (1-\alpha)(F-Y)).$$

By setting $\partial J / \partial F = 0$, we get $F = (1-\alpha)(I-\alpha W)^{-1} Y$.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C).

This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A processor-implemented method for preventing adverse drug-drug interactions by predicting drug-drug interactions based on clinical side effects, comprising:
   constructing a drug-drug interactions training dataset that includes pharmaceutical, pharmacokinetic or pharmacodynamics drug-drug interactions from any of a plurality of types of data sources for each of a plurality of drugs;
   constructing side effect features for each of the plurality of drugs based on determined clinical phenotypic side effects associated with each of the plurality of drugs;
   building, using the drug-drug interactions training dataset, a drug-drug interactions classifier that predicts adverse drug-drug interactions for drug pairs derivable from the clinical phenotypic side effects associated with the plurality of drugs, the building comprising:
      generating drug-drug interaction profiles of multiple drugs simultaneously using only a high-order network architecture structure by concatenating an initial label vector for each drug into an initial label matrix for each of the drug pairs,
      determining node influence scores for each node in the high-order network structure by minimizing a loss function by iteratively propagating the predicted drug-drug interaction information outwardly from a central node to a subset of directly neighboring nodes and thereafter to a subset of indirectly neighboring nodes until convergence of a classifying objective function, and
      predicting drug-drug interaction profiles for the drug-drug pairs based on the drug-drug interaction profiles and the node influence scores;
   for each of the side effects, building a two-by-two table using the side effect features and the predicted drug-drug interaction profiles, and performing a Fisher's exact test using the two-by-two table to determine whether a given one of side effects is differentially shown between positive predicted drug-drug interactions and negative predicted drug-drug interactions; and
   for any of the drug pairs having the given one of the side effects that, in turn, has one or more of the positive predicted drug-drug interactions representative of a potential adverse drug combination determined using the two-by-two table: (i) generating a drug label for corresponding drug containers that warns of the potential adverse drug combination, and (ii) generating, using a speaker operably coupled to the processor, a local adverse event warning of the potential adverse drug combination.

2. The method of claim 1, wherein the multiple data sources comprise at least one of a drug bank, drug label information, an adverse event reporting system, and text mining from scientific documents.

3. The method of claim 1, wherein the side effects, from which the side effect features are constructed, are determined from at least one of clinical trials, drug development information, empirical information, drug labels, and an adverse event reporting system.

4. The method of claim 1, wherein each of the side effects is designated as a respective one of the side effect features, and each of the drug pairs is represented as a vector of side effect features having either a first value, a second value, or a third value respectively indicating that the drugs forming a particular drug pair have zero side effects, only one of the drugs has side effects, and both of the drugs have side effects.

5. The method of claim 1, wherein the side effect features used for building the drug-drug interactions classifier comprise at least one of drug clinical side effect keywords, and drug properties.

6. The method of claim 5, wherein the drug properties comprise at least one of chemical structures and protein targets.

7. The method of claim 1, wherein building the drug-drug interactions classifier comprises using a label propagation method.

8. The method of claim 7, wherein label propagation method propagates drug-drug interactions between different ones of the plurality of drugs on a basis that if a first drug has an interaction with a second drug and the second drug is similar to a third drug, then the first drug will be considered to have also the interaction with the third drug.

9. The method of claim 7, wherein the label propagation method is performed using a similarity graph comprising a plurality of nodes and a plurality of edges connecting the plurality of nodes, each of the plurality of nodes being associated with a respective drug from the plurality of drugs and including drug-drug interactions information for the drug pairs that include the respective drug, and each of the plurality of edges for propagating the drug-drug interactions information between the plurality of nodes.

10. The method of claim 9, wherein the similarity graph is constructed to have, from among the plurality of nodes, a central node, a plurality of directly neighboring nodes with respect to the central node, and a plurality of indirectly neighboring nodes with respect to the central node.

11. The method of claim 1, wherein the drug-drug interactions classifier uses the classifying objective function to render the predicted adverse drug-drug interactions, the classifying objective function having a smoothness constraint and a fitting constraint.

12. A computer program product for preventing adverse drug-drug interactions by predicting drug-drug interactions based on clinical side effects, the computer program product comprising a computer readable storage medium having program instructions embodied therewith, the program instructions executable by a computer to cause the computer to perform a method comprising:
   constructing a drug-drug interactions training dataset that includes pharmaceutical, pharmacokinetic or pharmacodynamics drug-drug interactions from any of a plurality of types of data sources for each of a plurality of drugs;
   constructing side effect features for each of the plurality of drugs based on determined clinical phenotypic side effects associated with each of the plurality of drugs;
   building, using the drug-drug interactions training dataset, a drug-drug interactions classifier that predicts adverse drug-drug interactions for drug pairs derivable from the clinical phenotypic side effects associated with the plurality of drugs, the building comprising:

generating drug-drug interaction profiles of multiple drugs simultaneously using only a high-order network architecture structure by concatenating an initial label vector for each drug into an initial label matrix for each of the drug pairs, determining node influence scores for each node in the high-order network structure by minimizing a loss function by iteratively propagating the predicted drug-drug interaction information outwardly from a central node to a subset of directly neighboring nodes and thereafter to a subset of indirectly neighboring nodes until convergence of a classifying objective function, and predicting drug-drug interaction profiles for the drug-drug pairs based on the drug-drug interaction profiles and the node influence scores;

for each of the side effects, building a two-by-two table using the side effect features and the predicted drug-drug interaction profiles, and performing a Fisher's exact test using the two-by-two table to determine whether a given one of side effects is differentially shown between positive predicted drug-drug interactions and negative predicted drug-drug interactions; and for any of the drug pairs having the given one of the side effects that, in turn, has one or more of the positive predicted drug-drug interactions representative of a potential adverse drug combination determined using the two-by-two table: (i) generating a drug label for corresponding drug containers that warns of the potential adverse drug combination, and (ii) generating, using a speaker operably coupled to the processor, a local adverse event warning of the potential adverse drug combination.

13. The computer program product of claim 12, wherein each of the side effects is designated as a respective one of the side effect features, and each of the drug pairs is represented as a vector of side effect features having either a first value, a second value, or a third value respectively indicating that the drugs forming a particular drug pair have zero side effects, only one of the drugs has side effects, and both of the drugs have side effects.

14. The computer program product of claim 12, wherein the side effect features used for building the drug-drug interactions classifier comprise at least one of drug clinical side effect keywords, and drug properties.

15. The computer program product of claim 12, wherein building the drug-drug interactions classifier comprises using a label propagation method.

16. The computer program product of claim 15, wherein label propagation method propagates drug-drug interactions between different ones of the plurality of drugs on a basis that if a first drug has an interaction with a second drug and the second drug is similar to a third drug, then the first drug will be considered to have also the interaction with the third drug.

17. The computer program product of claim 15, wherein the label propagation method is performed using a similarity graph comprising a plurality of nodes and a plurality of edges connecting the plurality of nodes, each of the plurality of nodes being associated with a respective drug from the plurality of drugs and including drug-drug interactions information for the drug pairs that include the respective drug, and each of the plurality of edges for propagating the drug-drug interactions information between the plurality of nodes.

18. The computer program product of claim 17, wherein the similarity graph is constructed to have, from among the plurality of nodes, a central node, a plurality of directly neighboring nodes with respect to the central node, and a plurality of indirectly neighboring nodes with respect to the central node.

19. A system for preventing adverse drug-drug interactions by predicting drug-drug interactions based on clinical side effects, comprising:

a processor, configured for:

constructing a drug-drug interactions training dataset that includes pharmaceutical, pharmacokinetic or pharmacodynamics drug-drug interactions from any of a plurality of types of data sources for each of a plurality of drugs;

constructing side effect features for each of the plurality of drugs based on determined clinical phenotypic side effects associated with each of the plurality of drugs;

building, using the drug-drug interactions training dataset, a drug-drug interactions classifier that predicts adverse drug-drug interactions for drug pairs derivable from the clinical phenotypic side effects associated with the plurality of drugs, the building comprising:

generating drug-drug interaction profiles of multiple drugs simultaneously using only a high-order network architecture structure by concatenating an initial label vector for each drug into an initial label matrix for each of the drug pairs, determining node influence scores for each node in the high-order network structure by minimizing a loss function by iteratively propagating the predicted drug-drug interaction information outwardly from a central node to a subset of directly neighboring nodes and thereafter to a subset of indirectly neighboring nodes until convergence of a classifying objective function, and predicting drug-drug interaction profiles for the drug-drug pairs based on the drug-drug interaction profiles and the node influence scores;

for each of the side effects, building a two-by-two table using the side effect features and the predicted drug-drug interaction profiles, and performing a Fisher's exact test using the two-by-two table to determine whether a given one of side effects is differentially shown between positive predicted drug-drug interactions and negative predicted drug-drug interactions; and for any of the drug pairs having the given one of the side effects that, in turn, has one or more of the positive predicted drug-drug interactions representative of a potential adverse drug combination determined using the two-by-two table: (i) generate a drug label for corresponding drug containers that warns of the potential adverse drug combination, and (ii) generate, using a speaker operably coupled to the processor, a local adverse event warning of the potential adverse drug combination.

* * * * *